(12) United States Patent
Bidoia

(10) Patent No.: US 6,179,855 B1
(45) Date of Patent: Jan. 30, 2001

(54) DEVICE FOR PROTECTING THE TISSUES OF PHYSIOLOGICAL PATHWAYS DURING EXPLORATIONS WITH DIAGNOSTIC AND/OR OPERATING INSTRUMENTS

(75) Inventor: Gianfranco Bidoia, Padua (IT)

(73) Assignee: Bidoia S.a.s. di Gianfranco Bidoia E C., Vigonza (IT)

( * ) Notice: Under 35 U.S.C. 154(b), the term of this patent shall be extended for 0 days.

(21) Appl. No.: 09/189,994

(22) Filed: Nov. 12, 1998

(30) Foreign Application Priority Data

Nov. 18, 1997 (IT) .............................................. PD97A0265

(51) Int. Cl.$^7$ .................................................. A61M 29/00
(52) U.S. Cl. ............................................................... 606/192
(58) Field of Search .................................... 606/191, 213, 606/198, 108, 185; 604/54, 96, 264; 623/1; 600/573

(56) References Cited

U.S. PATENT DOCUMENTS

| 4,411,655 | * | 10/1983 | Schreck | 604/165 |
| 4,644,936 | * | 2/1987 | Schiff | 604/165 |
| 5,025,778 | | 6/1991 | Opie et al. . | |
| 5,217,001 | * | 6/1993 | Nakao et al. | 128/4 |
| 5,417,666 | | 5/1995 | Coulter . | |
| 5,496,345 | * | 3/1996 | Kieturakis et al. | 606/192 |
| 5,522,881 | * | 6/1996 | Lentz | 623/1 |
| 5,601,591 | * | 2/1997 | Edwards et al. | 606/198 |
| 5,865,826 | * | 2/1999 | Paul | 606/1 |
| 5,948,191 | * | 9/1999 | Solovay | 606/192 |

FOREIGN PATENT DOCUMENTS 0 770 365   5/1997   (EP) .

* cited by examiner

Primary Examiner—Michael Buiz
Assistant Examiner—(Jackie) Tan-Uyen T Ho
(74) Attorney, Agent, or Firm—Guido Modiano; Albert Josif; Daniel O'Byrne

(57) ABSTRACT

A device for protecting the tissues of a physiological pathway during explorations performed with diagnostic and/or operating instruments, comprising a thin sheet made of plastics which is rolled up so as to form a tuboid. The tuboid, when inserted in the pathway, elastically increases its diameter as a consequence of the insertion of one of the instruments therein.

10 Claims, 2 Drawing Sheets

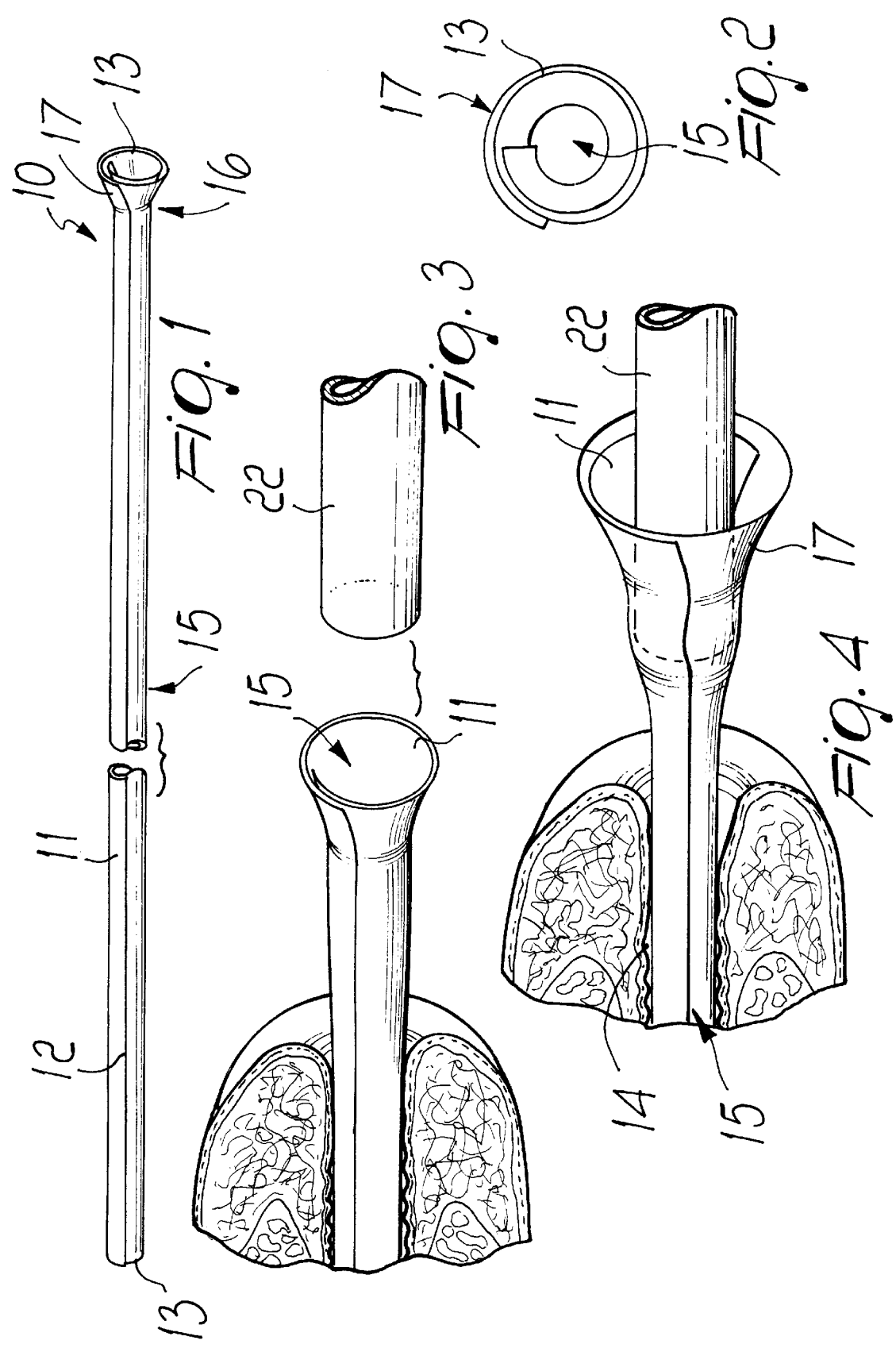

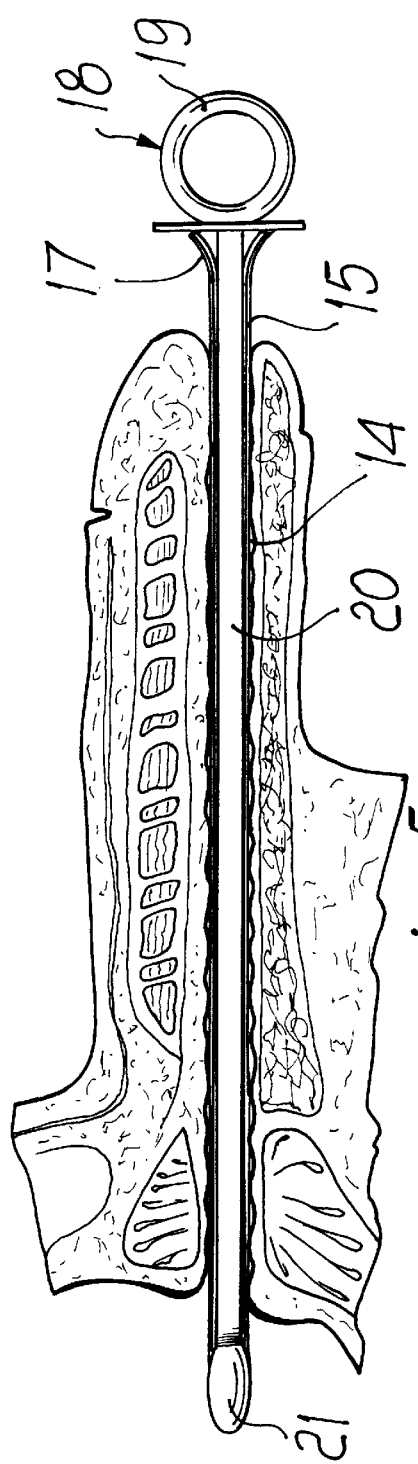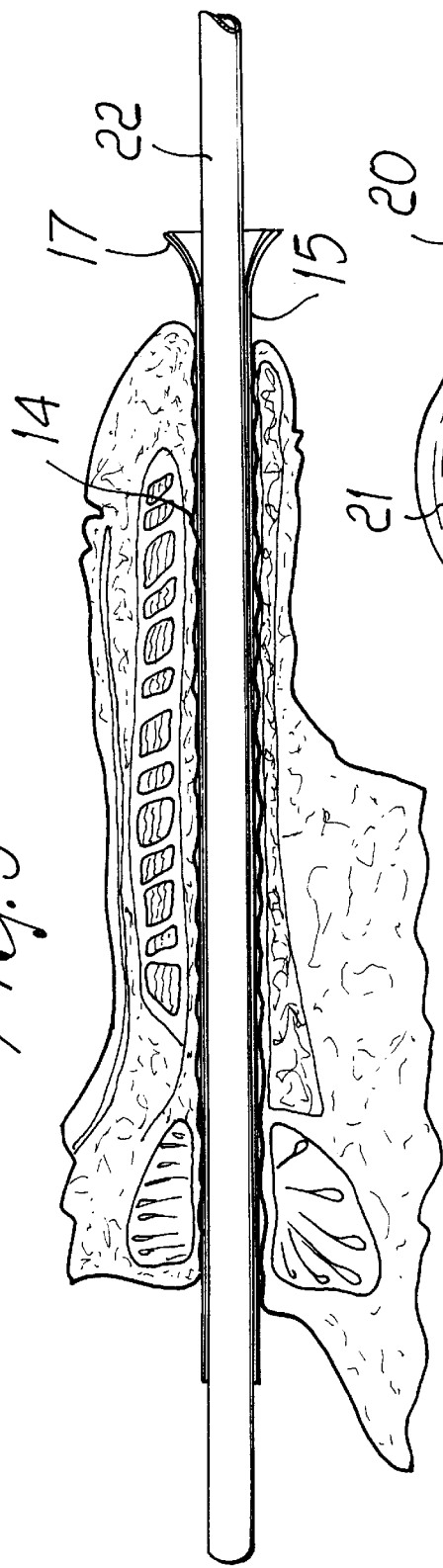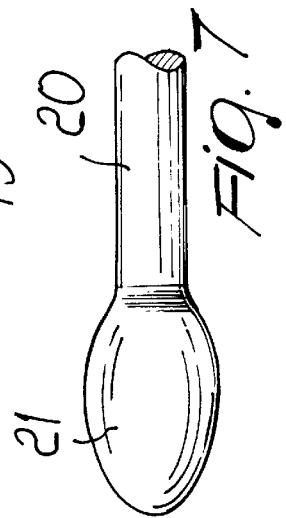

DEVICE FOR PROTECTING THE TISSUES OF PHYSIOLOGICAL PATHWAYS DURING EXPLORATIONS WITH DIAGNOSTIC AND/OR OPERATING INSTRUMENTS

BACKGROUND OF THE INVENTION

The present invention relates to a device for protecting physiological pathways subjected to explorations performed with diagnostic and/or operating instruments.

In medical work it is currently often necessary to explore and inspect organs of the human body by introducing particular instruments which use optical fibers in body passages.

This is the case in particular of urethroscopies, during which damage is usually caused to the tissues that compose the urethral canal through which the instruments pass in order to reach the bladder.

This is particularly evident when these passages are repeated at short intervals, for example to change the instrument, as usually occurs when replacing the diagnostic instrument with the operating instrument.

For example, it can also become necessary to insert a permanent catheter of the type known as the Foley catheter, which, despite being made of polyurethane, silicone, latex or other equivalent material and despite being inserted in the urethra with the aid of lubricants and of a thin rigid sound, can cause further damage to a tissue which has already suffered alterations and/or lacerations.

This damage is due to the particular concertina-like configuration of the tissue of the urethra, which does not form a true open canal but rather a canal which can be considered as such only once it is fully open and dilated by a foreign object.

Furthermore, in this case the tissue is more or less consistent and offers a variable resistance to the passage of the instrument, which is followed by the movement of the concertina-like mucous membrane.

The simple dilation of the canal actually produces very little or no damage.

On the contrary, the insertion of a foreign object having a considerable diameter causes important damage; for example, a diameter of 8 mm for an adult and 6 mm for children is sufficient.

Furthermore, if this insertion is repeated at closely spaced intervals, the damage can become more severe, although not permanent, and usually heals within 4–10 days, during which pain persists and is subsequently replaced by discomfort.

As a first step, the possibility of using a protective device substantially constituted by a tube of netting, capable of dilating when an instrument having a larger diameter than the tube passes, was considered.

However, such device unfortunately causes traumas in the tissue of the urethra when the netting, after elongating, returns to its original dimensions, entraining parts of the previously dilated tissue in the meshes that close.

Furthermore, since the meshes of the tube of netting are very thin in order to avoid increasing excessively the diameter of the passage canal, said meshes can become a sharp blade.

It should also be added that the netting tube does not allow the passage of a Foley catheter due to the presence therein of the Y-shaped union for inflating the balloon for retaining it.

Another drawback observed in the described netting tube occurs during elongation, when as the diameter increases the length of the tube decreases, but this variation is not acceptable.

A protective device obtained by mutually joining two half-tubes at two sides which can be semirigid or partially flexible was then considered.

However, this produces two parts which have different lengths according to the diameter to which they expand during the insertion of the instrument; moreover, it has been observed that the total diameter, constituted by the diameter of the instrument plus the diameter of the tube, increases considerably.

Even with this type of protective device, it is not possible to insert a Foley catheter for the same reasons mentioned for the netting tube.

SUMMARY OF THE INVENTION

The aim of the present invention is to provide a device for protecting the tissues of physiological pathways during explorations performed with diagnostic and/or operating instruments which solves all of the above mentioned drawbacks.

A consequent primary object of the present invention is to provide a protective device which can avoid direct contact between diagnostic or surgical instruments and the tissue of the pathway into which they must be inserted, thus avoiding as much as possible any damage thereto.

Another important object of the present invention is to provide a protective device which can be used easily.

Another important object is to provide a protective device which can be adapted to the various diameters of instruments.

Another object of the present invention is to provide a protective device whose insertion in the pathway to be protected causes no trauma to the tissue of said pathway.

Another object of the present invention is to provide a protective device for the tissues of a pathway of the human body which can be produced at a very low cost.

Another object of the present invention is to provide a protective device which allows to insert Foley catheters if it is inserted in the urethral canal.

This aim, these objects and others which will become apparent hereinafter are achieved by a device for protecting the tissues of a pathway of the human body during explorations performed with diagnostic and/or operating instruments, comprising a sheet made of plastics which is rolled up so as to form a tuboid which, when inserted in said pathway, increases its diameter by elongation and/or unrolling as a consequence of the insertion of one of said instruments therein.

BRIEF DESCRIPTION OF THE DRAWINGS

Further characteristics and advantages of the present invention will become apparent from the description of a preferred embodiment, illustrated by way of non-limitative example in the accompanying drawings, wherein:

FIG. 1 is a perspective view of a protective device according to the invention;

FIG. 2 is a front view of a detail of the device of FIG. 1;

FIG. 3 is a partial perspective view of the device of FIG. 1, during the preliminary insertion of an instrument;

FIG. 4 is a partial perspective view of the protective device of FIG. 3, partially dilated due to the insertion of said instrument;

FIG. 5 is a sectional view of the protective device of FIG. 1, fully inserted in the urethral canal by means of a stylet;

FIG. 6 is a sectional view of the protective device of FIG. 5 during full insertion of the exploratory instrument;

FIG. 7 is a perspective view of a detail of the stylet shown in FIG. 5.

DESCRIPTION OF THE PREFERRED EMBODIMENTS

With reference to the above listed figures, a device for protecting the tissues of a canal of the human body during explorations performed with a diagnostic and/or surgical instrument is generally designated by the reference numeral 10 and comprises a thin sheet 11 made of plastics.

The sheet 11 is flexible and has a rectangular shape which is elongated substantially longitudinally.

On the sheet 11 there are first longitudinal sides 12 and second transverse sides 13 which are smaller than the first ones 12.

In this example, the device 10 is adapted to be inserted in the urethral canal, schematically designated by the reference numeral 14, of a patient subjected for example to urethroscopy.

Preferably, the sheet 11 is made of medical-grade polyamide 66 or, as an alternative, of low-density polyethylene and has a thickness of 0.08–0.09 mm.

The sheet 11 is conveniently rolled up along its longitudinal extension so as to form a tuboid 15.

In this particular embodiment of the device 10 for urethroscopies, the tuboid 15 is obtained by means of two involutions of the sheet 11 and has an outside diameter of approximately 5.5 mm and an inside diameter of approximately 5.2 mm.

At a first end 16, the tube 15 is provided with a funnel-shaped blending portion 17 which is preferably formed by stretching the sheet 11 proximate to the corresponding second side 13 in a transverse direction.

The tuboid 15 can be easily inserted in the urethra 14 by means of a stylet 18 which is provided with a grip ring 19, from which a rod-like body 20 protrudes, and has, at the end of the rod-like body, an ogive 21 which is substantially olive-shaped.

The ogive 21 preferably has a diameter which is approximately two tenths of a millimeter greater than the outside diameter of the tuboid 15, while the diameter of the rod-like body 20 of the stylet 18 is approximately the same as the inside diameter of said tuboid 15.

The funnel-shaped blending portion 17 of the tuboid 15 prevents in any case accidental full insertion of the tuboid 15 in the urethral canal 14 and simultaneously facilitates the insertion of a diagnostic or surgical instrument, schematically designated by the reference numeral 22, which has a larger diameter than the tuboid 15 when not in use.

The tuboid 15 can in fact expand its diameter, adapting it to the diameter of the instrument 22, with a simple sliding of its longitudinal extension until, when unrolling is almost complete, it reaches a diameter of approximately 11 mm which is amply adequate for the passage of any exploratory or surgical instrument.

The insertion of the tuboid 15 in the canal 14 occurs nontraumatically by using the stylet 18.

The rod-like body 20 of the stylet in fact, by having a diameter which corresponds to the inside diameter of the tuboid 15, prevents the tuboid from moving, during insertion, in ways which may convert it into an element which can cause trauma to the urethral canal 14.

Once the insertion of the tuboid 15 in the urethra 14 has been completed, the ogive 21 is extracted, moving in reverse through the internal canal formed by the tuboid 15, which remains inserted.

Once this has been done, the device 10 is correctly positioned and is ready to facilitate the passage of the diagnostic and/or operating instrument 22, ensuring the fullest protection of the canal 14.

When the instrument 22 passes, the diameter of the tuboid 15 in fact expands, adapting to the diameter of the instrument 22 and avoiding direct contact thereof with the tissues of the canal 14.

The device 10 allows, in this particular configuration, the insertion of a Foley catheter, since it does not interfere with the Y-shaped union thereof.

It is important to stress the fact that the outside and inside diameter of the tuboid 15 and its thickness can be different according to the use or to the instruments for which it is provided.

The protective device described with the present invention is in fact not limited to specific urological use but can be applied to any other use in which it is necessary to protect delicate walls during the passage of bodies whose diameters are larger than said tuboid or parts that can cause lesions, irritations or other damage even in holes or openings provided artificially.

Furthermore, the use of a sheet or barrier made of plastic material between the surgical instrument and the human mucous membrane and/or tissue prevents the latter from suffering further lesions caused by electric discharges or dispersions during the use of instruments and/or systems for coagulation or electrical cutting.

The device can be made of materials having different chemical compositions as most appropriate in relation to the specific use as protection and for preventing direct contact between the passing element and the pathway in which it is passing.

The present invention is susceptible of numerous modifications and variations, all of which are within the scope of the same inventive concept.

All the details may furthermore be replaced with other technically equivalent elements.

The materials used, so long as they are compatible with the contingent use, as well as the dimensions, may be any according to the requirements.

The disclosures in Italian Patent Application No. PD97A000265 of Nov. 18, 1997 from which this application claims priority are incorporated herein by reference.

What is claimed is:

1. A device for protecting the tissues of a pathway of the human body during explorations performed with diagnostic and/or operating instruments, comprising a sheet made of plastics which is rolled up so as to form a tuboid which, when inserted in said pathway, increases its diameter from an initial configuration to an expanded configuration by elongation and/or unrolling as a consequence of the insertion of one of said instruments therein, said sheet having a pair of longitudinal sides and said sheet being rolled up such that in said initial configuration one of said longitudinal sides being arranged internally of said rolled up sheet and said sheet wrapping over said one of said longitudinal sides and another of said longitudinal sides being arranged externally of said rolled up sheet, and said rolled up sheet having an initial diameter when in said initial configuration, and said rolled up sheet having an expanded diameter larger than said initial diameter when in said expanded configuration.

2. The protective device according to claim 1, wherein said sheet has a rectangular shape and is rolled up at least twice so as to form said tuboid.

3. The protective device according to claim 2, wherein said funnel-shaped blending portion is formed by means of transverse elongations of one end of said plastic sheet.

4. The protective device according to claim 1, wherein said plastic sheet is 0.08 to 0.09 mm thick.

5. The protective device according to claim 1, wherein said tuboid has an inside diameter of approximately 5.2 mm and an outside diameter of approximately 5.5 mm.

6. The protective device according to claim 1, wherein said sheet is made of polyamide-66.

7. The protective device according to claim 1, wherein said sheet is made of low-density polyethylene.

8. The protective device according to claim 4, wherein said tuboid, in its almost fully widened configuration, reaches a diameter of approximately 11 mm.

9. A combination of a protective device for protecting the tissues of a pathway of the human body during explorations performed with diagnostic and/or operating instruments, and a stylet for the insertion of said protective device in a physiological pathway, said protective device comprising a sheet made of plastics which is rolled up so as to form a tuboid which, when inserted in said pathway, increases its diameter from an initial configuration to an expanded configuration by elongation and/or unrolling as a consequence of the insertion of one of said instruments therein, said sheet have a pair of longitudinal sides and said sheet being rolled up such that in said initial configuration one of said longitudinal sides being arranged internally of said rolled up sheet and said sheet wrapping over said one of said longitudinal sides and another of said longitudinal sides being arranged externally of said rolled up sheet, and said rolled up sheet having an initial diameter when in said initial configuration, and said rolled up sheet having an expanded diameter larger than said initial diameter when in said expanded configuration, and said stylet comprising a grip element from which a flexible rod-like element extends having a wider free end so as to form a bulb which is blended with the remaining part of the rod-like element.

10. The combination of claim 9, wherein said wider free end of said stylet has an ellipsoid shape.

* * * * *